(12) United States Patent
Onishi et al.

(10) Patent No.: US 6,338,957 B2
(45) Date of Patent: Jan. 15, 2002

(54) METHOD FOR PRODUCING HALO-L-TRYPTOPHAN

(75) Inventors: Norimasa Onishi; Kenzo Yokozeki, both of Kanagawa-ken (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 09/800,885

(22) Filed: Mar. 8, 2001

(30) Foreign Application Priority Data

Mar. 9, 2000 (JP) ............................................. 12-64276

(51) Int. Cl.⁷ ................................................ C12P 13/22
(52) U.S. Cl. ...................... 435/108; 435/170; 435/822; 435/873
(58) Field of Search ................................ 435/108, 170, 435/893

(56) References Cited

U.S. PATENT DOCUMENTS

| 4,335,209 A | 6/1982 | Asai et al. |
| 4,349,627 A | * 9/1982 | Mimura et al. ............. 435/108 |
| 4,360,594 A | 11/1982 | Mimura et al. |

FOREIGN PATENT DOCUMENTS

| FR | 1 207 437 | 2/1960 |
| JP | 52-9760 | 3/1977 |
| JP | 54-9760 | 1/1979 |
| JP | 62-134094 | 6/1987 |
| JP | 2000-64276 | 2/2000 |

OTHER PUBLICATIONS

Database WPI, Section Ch, Week 198730, Derwent Publications Ltd., London, GB; Class B02, AN 1987–208754, XP002171203, Jun. 17, 1987 (Abstract).

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

A method for producing halo-L-tryptophan from haloindole, comprising culturing a microorganism in a culture medium and then contacting the microorganism with (a) a mixture comprising haloindole, pyruvic acid and ammonia, or (b) a mixture comprising haloindole, a source of pyruvic acid and ammonia, until the halo-L-tryptophan is produced; and recovering the halo-L-tryptophan.

14 Claims, No Drawings

METHOD FOR PRODUCING HALO-L-TRYPTOPHAN

BACKGROUND OF THE INVENTION

1. Field of the Invention

The present invention relates to a method for preparing halo-L-tryptophan from haloindole using a microorganism.

2. Discussion of the Background

Halo-L-tryptophan, for example 5-chloro-L-tryptophan, is useful as a raw material for pharmaceutical products and as a synthetic intermediate for pharmaceutical products.

Methods for producing L-tryptophan from indole using microorganisms include a method using *Escherichia coli* (French Patent No. 1207437) and a method using a microorganism belonging to the genera *Proteus, Erwinia*, Pseudomonas or Aerobacter (Japanese Patent Publication No. 46348/1972). Methods for producing 5-hydroxy-L-tryptophan from 5-hydroxyindole include a method using a microorganism belonging to the genera Proteus, Erwinia, Pseudomonas or Aerobacter (Japanese Patent Publication No. 46348/1972) as well as methods using microorganisms such as *Bacillus subtilis, Corynebacterium hydrocarboclustus, Arthrobacter paraffinens, Micrococcus ureae, Brevibacterium ketoglutamicum, Hansenula anomala* and *Candida tropicalis* (Japanese Patent Publication No. 46349/1972). Additionally, a method for producing 5-amino-L-tryptophan from 5-aminoindole or for producing 5-methyl-L-tryptophan from 5-methylindole is also known (Japanese Patent Publication No. 9760/1977).

Generally, optically active halo-L-tryptophan can be produced by the combination of a chemical synthesis of N-acetyl-halo-DL-tryptophan and the optical resolution of halo-L-tryptophan by aminoacylase, that is, preparing halo-DL-tryptophan by a chemical synthetic method and subsequently acetylating halo-DL-tryptophan into N-acetylhalo-DL-tryptophan, which is further subjected to an optical resolution method with aminoacylase. However, the method requires complicated processes and the presence of residual N-acetyl-halo-D-tryptophan is disadvantageous.

No method is known for producing halo-L-tryptophan from haloindole. Accordingly, there remains a need for an method for producing halo-L-tryptophan from haloindole on an industrially efficient scale which overcomes the disadvantages of the known methods for preparing halo-L-tryptophan.

SUMMARY OF THE INVENTION

The present invention relates to a method for preparing a halo-L-tryptophan using a microorganism.

In particular, the present invention relates to a method for preparing halo-L-tryptophan comprising contacting a haloindole with a microorganism capable of producing halo-L-tryptophan from (a) a mixture comprising haloindole, pyruvic acid and ammonia; or (b) a mixture comprising haloindole and a source of pyruvic acid and ammonia.

In another embodiment, the present invention relates to a method for preparing of halo-L-tryptophan wherein L-tryptophan or a surfactant are also present in a culture medium.

The present inventor has considered that pyridoxal-5'-phosphate is the coenzyme of the enzyme that is involved in the present invention. The inventor have also considered that the molecule of pyridoxal-5'-phosphate might be removed from the enzyme during the cell collection. Therefore, the inventor has added pyridoxal-5'-phosphate into the reaction mixture to supplement the coenzyme. However, in another experiment, the inventor has found that supplementation of pyridoxal-5'-phosphate is not necessary for the present invention.

L-tryptophan is added into the culture medium. The inventor has found that the enzyme is induced by L-trypotphan and added it into the culture medium, not the reaction mixture. Surfactant is also added into the culture medium. The inventor has found that the enzyme converts L-tryptophan into indole (the reverse reaction) and the resulting indole has toxic effects on the cells. The surfactant surrounds the indole to form a micelle, thereby rendering it non-toxic. Therefore, the surfactant is not added into the reaction mixture.

In another embodiment, the present invention relates to a method for preparing a halo-L-tryptophan wherein L-tryptophan or a surfactant are also present in the culture medium.

A more complete appreciation of the invention and many of the attendant advantages thereof will be readily obtained as the same becomes better understood by reference to the following detailed description.

DETAILED DESCRIPTION OF THE INVENTION

The microorganism employed in the present invention may be any microorganism capable of producing halo-L-tryptophan at a high optical purity from (a) a combination of haloindole, pyruvic acid and ammonia; or (b) a combination of haloindole and a source supplying pyruvic acid and ammonia. The source providing pyruvic acid and ammonia may be L-serine, L-cysteine, O-methyl-L-serine, O-benzyl-L-serine, S-methylcysteine, S-benzylcysteine, for example.

The microbial materials, regardless of origin or purity, may be employed as cells in the free state or as cells immobilized on a support such as by physical adsorption or entrapment. Immobilized cells or immobilized treated cell matter can be used, for example, by using entrapment in carrageenan or polyacrylamide or adsorption onto membranes of polyether sulfone or regenerated cellulose, for example. When intact cells are used in the present invention, the culture per se or intact bacterial cells collected from the culture may be used. The microbial cells may be used in the form of dried cells such as lyophilized, spray-dried or heat-dried cells, or in the form of treated cell matter.

As used herein, the term "treated cell matter" means the biological material, such as cell walls, membranes, nuclei, proteins, etc. which result from the subjection of intact cells to mechanical or chemical disruption. Preferred methods of disrupting intact cells by mechanical means include disruption by ultrasonication, glass beads, pressing and freeze-drying. Pressing in a French Press is particularly preferred. Preferred methods of disrupting intact cells by chemical means include disruption by lytic enzymes, organic solvents and surfactants. Following mechanical or chemical disruption the cell fragments and other cellular debris are removed by centrifugation or membrane filtration.

Crude enzyme fractions or purified enzymes prepared from the disruption of intact cells can also be used in the method of the invention, satisfactorily, when the enzyme fractions or purified enzymes retain the essential activity, and include crude enzyme fractions or purified enzymes prepared from treated cell matter.

Exemplary microorganisms for use in the invention include those belonging to the following genera which may be isolated from natural origins, such as plant or soil material: Proteus, Providencia and Morganella. Particularly preferred microorganisms are those species within the genus Proteus, such as *Proteus vulgaris* ATCC 13315, *Proteus mirabilis* ATCC 29906, *Proteus myxofaciens*, ATCC 19692 and *Proteus penneri* ATCC 33519. Particularly preferred microorganisms are also those species within the genus Providencia, such as *Providencia stuartii* ATCC 33672. Particularly preferred microorganisms are those species within the genus Morganella, such as *Morganella morganii* ATCC 8019.

It should be understood that mutants of the biologically pure microorganisms are also contemplated by the present invention for use in the methods described herein, such as those modified by the use of chemical, physical (for example, x-rays) or biological means (for example, molecular biology techniques).

Growth of the microorganisms may be achieved by one of ordinary skill in the art without undue experimentation by the use of an appropriate medium, including solid and liquid media. Methods for culturing the microorganisms in accordance with the invention can be facilitated in conventionally used culture media, namely culture media containing a carbon source, nitrogen source, inorganic salts, trace metal salts, and vitamins. Furthermore, depending on the species or culture conditions of the microorganism, the ability to produce halo-L-tryptophan can be promoted by adding L-tryptophan at a concentration of about 1.0 to 10.0 g/l to the culture media. This range includes all specific values and sub-ranges there between, such as, but not limited to, 1.5, 2, 2.5, 3, 4, 5, 7 and 9 g/l. Furthermore, physiologically acceptable surfactants such as Triton X100 and olive oil may be added to the culture media, which sometimes serve to enhance the ability of the microorganisms to produce halo-L-tryptophan. As specific substances for use as the ingredients in the culture media, carbon sources such as glucose and sucrose, polyols such as glycerol, organic acids such as succinic acid, citric acid and fumaric acid, or mixtures thereof can be used. As the nitrogen source, ammonium sulfate, ammonium chloride, urea, yeast extract, meat extract, corn steep liquor and casein hydrolysate, or mixtures thereof can be used. As specific compositions of the culture media, for example, a culture medium containing 5 g/l succinic acid, 10 g/l casamino acid, 3 g/l yeast extract, 60 ml/l corn steep liquor, 5 g/l L-tryptophan, 5 g/l $K_2HPO_4$, 0.5 g/l $MgSO_4 \cdot 7H_2O$, 0.01 g/l $FeSO_4 \cdot 7H_2O$, 0.01 g/l $MnSO_4 \cdot 4H_2O$, and 50 g/l Triton X100, pH 7.0.

The culture temperature to be used is within a range which the microorganism can generally grow, namely a range of 20 to 45° C., preferably a range of 25 to 37° C. This range includes all specific values and sub-ranges there between, such as, but not limited to, 21, 22, 23, 25, 27, 29, 30, 35, 37, 40 and 43° C. Additionally, the culture media are adjusted within a range of pH 3 to 11, preferably within a range of pH 4 to 8. This range includes all specific values and sub-ranges there between, such as, but not limited to, pH 3.5, 4.5, 5, 5.5, 6, 6.5, 7, 9 and 10. Aeration conditions are set to aerobic or anaerobic conditions suitable for the growth of the microorganism to be used. The culture period is generally 12 to 120 hours, preferably about 24 to 96 hours. This range includes all specific values and sub-ranges there between, such as, but not limited to, 15, 20, 30, 40, 50, 60, 70, 80, 90, 100 and 110 hours.

Raw materials for the production of halo-L-tryptophan, namely a combination of haloindole and pyruvic acid and ammonia, or a combination of haloindole and a source supplying pyruvic acid and ammonia, such as L-serine, is collectively, intermittently or continuously added to the culture media. The raw materials can be added directly to the culture of the bacteria or can be added to the reaction mixture suspended with the cells or the treated cell matter separated from the culture. The substrates are added in the state of aqueous solution or slurry. To increase their solubility and to promote their dispersion, the substrates may be mixed with physiologically acceptable organic solvents and surfactants. Additionally, a remarkable outcome may sometimes be brought about when pyridoxal 5'-phosphate is added at a concentration of from 0.01 mg/ml to 0.3 mg/ml. This range includes all specific values and sub-ranges there between, such as, but not limited to, 0.02, 0.03, 0.05, 0.075, 0.1, 0.15, 0.2, 0.25, 0.275 mg/ml.

To produce halo-L-tryptophan using the culture method, raw materials for producing halo-L-tryptophan are added to the culture, as they are, so as to continue the culturing. Any amount of haloindole can be added, with no limitation. However, the amount is generally at a concentration of 1 g/l to 200 g/l. This range includes all specific values and sub-ranges there between, such as, but not limited to, 2, 5, 10, 20, 40, 50, 100, 150 and 175 g/l. In this case, the pH of the culture medium after addition of the raw materials is adjusted to about pH 8.4 to 9.0, which works to enhance the productivity of halo-L-tryptophan.

To produce halo-L-tryptophan using cells isolated from culture the bacteria are first separated from the culture medium and then suspended or dissolved together with the raw materials including haloindole in aqueous media, to produce halo-L-tryptophan. Haloindole can be used at any amount with no specific limitation, which is generally adjusted to a concentration of 1 g/l to 200 g/l. This range includes all specific values and sub-ranges there between, such as, but not limited to, 2, 5, 10, 20, 40, 50, 100, 150 and 175 g/l. The reaction is carried out at a temperature of 20 to 60° C., preferably within a range of 30 to 45° C. This range includes all specific values and sub-ranges there between, such as, but not limited to, 25, 30, 35, 40, 45, 50 and 55° C. Additionally, the reaction solution is adjusted to a range of pH 7 to 11, preferably pH 8 to 9.5. This range includes all specific values and sub-ranges there between, such as, but not limited to, pH 7.3, 7.5, 7.8, 8.0, 8.5, 9.0, 9.5, 10 and 10.5. The reaction time is generally one to 120 hours, preferably about 6 to 96 hours. This range includes all specific values and sub-ranges there between, such as, but not limited to, 2, 5, 10, 20, 30, 40, 50, 75, 100 and 110 hours.

The resulting halo-L-tryptophan can be determined quantitatively by well-known methods in a rapid manner. More specifically, high performance liquid chromatography on an ODS column is satisfactorily used. For the determination of optical purity, high performance liquid chromatography using an optical resolution column such as CROWNPAK CR (+) manufactured by Daicel Chemical Industry may satisfactorily be used. The halo-L-tryptophan which accumulates in the culture medium or the reaction solution can be collected from the culture or the reaction solution by conventional methods. The halo-L-tryptophan can be collected from the culture or the reaction solution by methods conventionally known. Procedures such as filtration, centrifugation, concentration in vacuum, solvent extraction, ion exchange or adsorption chromatography and crystallization are appropriately combined together and used, depending on the need.

EXAMPLES

Having generally described this invention, a further understanding can be obtained by reference to certain specific examples which are provided herein for purposes of illustration only and are not intended to be limiting unless otherwise specified.

In the examples herein, HPLC determination and optical purity determination are carried out under the following conditions.

Determination
- Column: Inertsill ODS-2 (Φ4.6×250 mm; manufactured by GL Science, Co.) Mobile phase: water adjusted to pH 2.0, with addition of phosphoric acid/acetonitrile× 1/1 (V/V)
- Flow rate: 0.5 ml/min
- Column temperature: 25° C.
- Detection: UV 254 nm Optical purity determination
- Column: CROWNPAK CR (+) (Φ4.6×150 mm; manufactured by Daicel, Co.)
- Mobile phase: aqueous perchloric acid, pH 2.0/methanol= 85/15 (V/V)
- Flow rate: 0.5 ml/min
- Column temperature: 45° C.
- Detection: UV 254 nm.

Example 1

A culture medium containing 5 g/l succinic acid, 10 g/l casamino acid, 3 g/l powdered yeast extract, 60 ml/l corn steep liquor, 5 g/l L-tryptophan, 5 g/l $K_2HPO_4$, 0.5 g/l $MgSO_4$, $7H_2O$, 0.01 g/l $FeSO_4$. $7H_2O$, 0.01 g/l $MnSO_4$. $4H_2O$, and 50 g/l Triton X100, pH 7.0, was divided into 50 ml portions in a 500 ml Sakaguchi flask and sterilized at 120° C. for 10 minutes. After cooling, an appropriate inoculum, such as one platinum spoon, of each microorganism shown in Table 1 which had been cultured on a bouillon agar plate at 30° C. for 24 hours was inoculated into the above medium in a 500 ml Sakaguchi flask under aerobic shaking at 30° C. for 16 hours. After subsequent centrifugation (18,000×g for 10 minutes), the bacteria were collected and suspended in water, to prepare a 5 ml cell suspension. A 50 ml of solution containing 80 mg/ml sodium pyruvate, 80 mg/l ammonium acetate, 8 mg/ml sodium sulfite and 0.2 mg/ml pyridoxal 5'-phosphate was adjusted to pH 8.8, using potassium hydroxide solution, to adjust the final volume to 80 ml (substrate solution A). Subsequently, each 1 ml of cell suspension was added to the 8 ml of substrate solution A, to which was added 1 ml of a 200 mg/ml solution containing 5-fluoroindole dissolved in methanol, for incubation at 37° C. After 24-hour reaction, the reaction was stopped with boiling for 5 minutes. The amount of 5-fluoro-L-tryptophan produced in the reaction solution is shown in Table 1.

TABLE 1

| Strains | Amount of 5-fluoro-L-tryptophan produced (g/l) |
| --- | --- |
| Proteus vulgaris ATCC 13315 | 20.3 |
| Proteus mirabilis ATCC 29906 | 5.2 |
| Proteus myxofaciens ATTC 19692 | 4.5 |
| Proteus penneri ATCC 33519 | 4.2 |
| Providencia stuartii ATCC 33672 | 17.8 |
| Morganella morganii ATCC 8019 | 3.4 |
| Bacillus subtilis ATCC 13962 (Comparative Example) | 0 |
| Brevibacterium ketoglutamicum ATCC 15587 (Comparative Example) | 0 |
| Enterobacter cloacae ATCC 7256 (Comparative Example) | 0 |

Example 2

In the same manner as in Example 1, the cell suspension of Proteus vulgaris ATCC 13315 was prepared. Subsequently, 50 ml of a solution containing 120 mg/ml L-serine, 8 mg/ml sodium sulfite and 0.2 mg/ml pyridoxal 5'-phosphate were adjusted to pH 8.8, using potassium hydroxide solution, to adjust the final volume to 80 ml (substrate solution B). Subsequently, 1 ml of cell suspension was added to the 8 ml of substrate solution B, to which was added 1 ml of a solution containing 200 mg/ml 5-fluoroindole dissolved in methanol, and was incubated at 37° C. After the reaction had proceeded for the times indicated in Table 2, the reaction was stopped with boiling for 5 minutes. The amount of 5-fluoro-L-tryptophan produced in the reaction solution for 2, 6, 18 and 30 hours of reaction is shown in Table 2.

TABLE 2

| Reaction time | Amount of 5-fluoro-L-tryptophan produced (g/l) |
| --- | --- |
| 0 | 0 |
| 2 | 9.6 |
| 6 | 14.3 |
| 18 | 25.2 |
| 30 | 26.2 |

Example 3

In the same manner as in Example 1 in a reaction solution of a volume of 50 ml using Providencia stuartii ATCC 33672, 5-fluoro-L-tryptophan was produced in the reaction solution. Subsequently, water was added to the reaction solution to a final total volume of 400 ml, which was boiled at 100° C. for 10 minutes to thoroughly dissolve the produced 5-fluoro-L-tryptophan and, the cells were then removed by centrifugation (18,000×g for 10 minutes). The supernatant was subjected to adsorption onto a synthetic adsorption resin SP207, which was then rinsed with 1,000 ml of 5% by weight of ethanol, and the 5-fluoro-L-tryptophan was then eluted with 500 ml of 30% by weight of ethanol. The eluted solution was concentrated to 50 ml with an evaporator at 50° C., followed by cooling at room temperature to crystallize the 5-fluoro-L-tryptophan. The resulting crystal was isolated and dried to recover a needle-like crystal of 390 mg. The optical purity of the resulting crystal was analyzed by high performance liquid chromatography on an optical resolution column CROWNPAK CR(+) manufactured by Daicel. Consequently, the optical purity was 99.3% e.e.

Example 4

In the same manner as in Example 2, a cell suspension of Proteus vulgaris ATCC 13315 and the substrate solution B were prepared. Subsequently, 1 ml of the cell suspension was added to 8 ml of the substrate solution B, followed by each addition of a 1 ml of solution containing 200 mg/ml 4-fluoroindole, 6-fluoroindole, 4-chloroindole, 5-chloroindole, 6-chloroindole, 7-chloroindole or 5-bromoindole in methanol, and the preparation was then incubated at 37° C. for 24 hours. After the reaction, reaction was stopped with boiling for 5 minutes. The amounts of the resulting halo-L-tryptophan produced in each reaction solution are shown in Table 3.

TABLE 3

| Products | Amounts of products (g/l) |
| --- | --- |
| 4-fluoro-L-tryptophan | 18.2 |
| 6-fluoro-L-tryptophan | 30.0 |
| 4-chloro-L-tryptophan | 5.1 |
| 5-chloro-L-tryptophan | 11.1 |
| 6-chloro-L-tryptophan | 18.3 |
| 7-chloro-L-tryptophan | 3.0 |
| 5-bromo-L-tryptophan | 2.0 |

This application is based on Japanese Patent Application No. 64276/2000, filed Mar. 9, 2000, the entire contents of which are hereby incorporated by reference herein, the same as if they were fully set forth at length.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for producing a halo-L-tryptophan from a haloindole, comprising:
    culturing a microorganism which (1) belongs to the genus Proteus, (b) is *Morganella morganii* or (c) is *Providentia stuartii* in a culture medium and then contacting the microorganism with
        (a) a mixture comprising a haloindole, pyruvic acid and ammonia; or
        (b) a mixture comprising a haloindole and a source of pyruvic acid and ammonia; until the halo-L-tryptophan is produced; and
    recovering the halo-L-tryptophan.

2. A method according to claim 1, wherein the microorganism belongs to the genus Proteus.

3. A method according to claim 2, wherein the microorganism is selected from the group consisting of *Proteus vulgaris, Proteus mirabilis, Proteus myxofaciens*, and *Proteus penneri*.

4. A method according to claim 1, wherein the source of pyruvic acid and ammonia is selected from the group consisting of L-serine, L-cysteine, O-methyl-L-serine, O-benzyl-L-serine, S-methylcysteine and S-benzylcysteine.

5. A method according to claim 1, wherein the haloindole is a compound selected from the group consisting of 4-haloindole, 5-haloindole, 6-haloindole, and 7-haloindole.

6. A method according to claim 1, wherein the halo-L-tryptophan produced is a compound selected from the group consisting of 5-halo-L-tryptophan, 6-halo-L-tryptophan, and 7-halo-L-tryptophan.

7. A method according to claim 1, wherein treated cell material of the microorganism is contacted with the mixture.

8. A method according to claim 1, further comprising adding L-tryptophan to the culture medium.

9. A method according to claim 8, wherein L-tryptophan is present at a concentration of from 1 to 10 g/l.

10. A method according to claim 1, further comprising adding a surfactant to the culture medium.

11. A method according to claim 10, wherein the surfactant is selected from the group consisting of Triton X100 and olive oil.

12. A method according to claim 1, wherein the microorganism is immobilized on a support.

13. A method according to claim 12, wherein the support is selected from the group consisting of carrageenan, polyacrylamide, polyether sulfone and regenerated cellulose.

14. The method according to claim 1, wherein the microorganism is *Providentia stuartii*.

* * * * *